United States Patent
Brennen et al.

(10) Patent No.: US 6,632,400 B1
(45) Date of Patent: Oct. 14, 2003

(54) INTEGRATED MICROFLUIDIC AND ELECTRONIC COMPONENTS

(75) Inventors: Reid A. Brennen, San Rafael, CA (US); Antonius A. A. M. van de Goor, Foster City, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 265 days.

(21) Appl. No.: 09/599,401

(22) Filed: Jun. 22, 2000

(51) Int. Cl.[7] .................... G01N 27/00; G01N 27/27
(52) U.S. Cl. .............. 422/82.01; 422/99; 422/98; 422/102; 422/104; 204/600; 204/601; 204/602; 204/603; 204/452
(58) Field of Search ............... 422/82.01, 98, 422/100, 102; 204/601, 600, 602, 603, 452

(56) References Cited

U.S. PATENT DOCUMENTS

| | | | |
|---|---|---|---|
| 5,150,969 A | | 9/1992 | Goldberg et al. |
| 5,194,133 A | * | 3/1993 | Clark et al. .......... 204/403.01 |
| 5,258,097 A | * | 11/1993 | Mastrangelo .......... 216/39 |
| 5,291,066 A | * | 3/1994 | Neugebauer et al. ...... 257/750 |
| 5,293,877 A | | 3/1994 | O'Hara et al. |
| 5,469,855 A | | 11/1995 | Pompei et al. |
| 5,511,428 A | | 4/1996 | Goldberg et al. ........ 73/777 |
| 5,576,147 A | * | 11/1996 | Guckel et al. .......... 430/313 |
| 5,585,069 A | | 12/1996 | Zanzucchi et al. |
| 5,639,423 A | | 6/1997 | Northrup et al. |
| 5,640,995 A | * | 6/1997 | Packard et al. .......... 137/597 |
| 5,726,026 A | | 3/1998 | Wilding |
| 5,800,690 A | * | 9/1998 | Chow et al. ........... 204/451 |
| 5,824,204 A | * | 10/1998 | Jerman ............... 204/601 |
| 5,839,722 A | * | 11/1998 | Berlin et al. .......... 269/57 |
| 5,867,266 A | * | 2/1999 | Craighead ............. 356/344 |
| 5,876,582 A | * | 3/1999 | Frazier .............. 205/122 |
| 5,882,571 A | | 3/1999 | Kaltenbach et al. ..... 264/400 |
| 5,903,041 A | * | 5/1999 | La Fleur et al. ........ 257/530 |

(List continued on next page.)

FOREIGN PATENT DOCUMENTS

| | | |
|---|---|---|
| DE | 19648695 A | 6/1966 |
| DE | 19507638 A | 9/1996 |
| EP | 0969510 A2 | 6/1966 |
| EP | 0992287 A2 | 8/1999 |
| WO | WO98/50154 | 5/1998 |
| WO | WO98/38510 | 9/1998 |
| WO | WO98/50154 | 11/1998 |

OTHER PUBLICATIONS

Choi et al., "Planar Bio/Magnetic Bead Separator with Microfluidic Channel," SPIE Conference on Microfluidic Devices and Systems, SPIE vol. 3515, Sep. 1998, pp. 260–267.

(List continued on next page.)

*Primary Examiner*—Arlen Soderquist
*Assistant Examiner*—Elizabeth Quan

(57) ABSTRACT

A microfluidic component having a microfluidic channel is bonded to an electronics component having a circuit for processing signals related to the microfluidic component. In an embodiment, the electronics component is a prefabricated integrated circuit chip that includes signal processing and/or process control functionality. The bonding of the microfluidic component to the electronics component provides a modular architecture in which different combinations of microfluidic components and electronics components can be used to create customized processing and analysis tools.

14 Claims, 7 Drawing Sheets

U.S. PATENT DOCUMENTS

| | | | | |
|---|---|---|---|---|
| 6,048,734 | A | * | 4/2000 | Burns et al. ................. 436/180 |
| 6,136,212 | A | * | 10/2000 | Mastrangelo et al. .......... 216/27 |
| 6,167,910 | B1 | * | 1/2001 | Chow .......................... 137/526 |
| 6,193,471 | B1 | * | 2/2001 | Paul ............................. 417/53 |
| 6,254,827 | B1 | * | 7/2001 | Ackley et al. .............. 422/68.1 |
| 6,280,590 | B1 | * | 8/2001 | Cheng et al. ................ 204/463 |
| 6,326,160 | B1 | * | 12/2001 | Dunn et al. .................. 204/400 |
| 6,349,740 | B1 | * | 2/2002 | Cho et al. ................. 137/487.5 |
| 6,386,219 | B1 | * | 5/2002 | Barth et al. .............. 137/15.01 |
| 6,392,144 | B1 | * | 5/2002 | Filter et al. ................. 174/52.4 |
| 6,454,924 | B2 | * | 9/2002 | Jedrzejewski et al. ...... 204/601 |
| 6,458,615 | B1 | * | 10/2002 | Fedder et al. ................. 438/50 |

OTHER PUBLICATIONS

Kramer et al., "An Optical MEMS–based Fluorescence Detection Scheme with Applications to Capillary Electrophoresis," SPIE Conference on Microfluidic Devices and Systems, SPIE vol. 3515, Sep. 1998, pp. 76–85.

Mastrangelo et al., "Microfabricated Devices for Genetic Diagnostics," Proceedings of the IEEE, vol. 86, No. 8, Aug. 1998, pp. 1769–1787.

* cited by examiner

INTEGRATED MICROFLUIDIC AND ELECTRONIC COMPONENTS

TECHNICAL FIELD

The invention relates to microfabricated devices for chemical and biological analysis, and more particularly to the integration of microfluidic and electronic components.

BACKGROUND ART

Microfluidic technology is utilized to create systems that can perform chemical and biological analysis on a much smaller scale than previous techniques. A popular use of microfluidic systems is in the analysis of DNA molecules. Microfluidic systems for analysis, chemical and biological processing, and sample preparation may include some combination of the following elements: pre- and post-processing fluidic handling components, microfluidic components, microfluidic-to-system interface components, electrical and electronics components, environmental control components, and data analysis components.

As microfluidic systems reduce in size and increase in complexity, there is a growing need for electronic and electrical processing support to enhance the analysis capabilities. Known microfluidic systems provide electronic and electrical processing support by performing operations such as voltage/current sourcing, signal sourcing, signal detection, signal processing, signal feedback, and data processing separately from the microfluidic system. In some instances separation of the electronic processing and microfluidic functions is desirable. For example, a relatively large power supply is required in order to apply a high voltage to a microfluidic channel for electrophoresis, and it is best to locate the power supply separate from the microfluidic system. As another example, data analysis is best performed using a computer that is separate from the microfluidic system.

However, some electrical processes have requirements that are difficult to meet utilizing electrical components that are separate from the microfluidic system. For example, very low energy signals which are detected from microfluidic systems tend to degrade as they are conducted away from the microfluidic system to a separate signal processing component. As a result of the tendency for signal degradation, it is preferable to amplify the detected signals before they degrade. On-system electrical processing is also desired in cases where information gathered from many sensors on a microfluidic system must be used to control processes on the microfluidic chip. For example, a temperature system input might be used to control heaters of a microfluidic system.

One technique for providing signal detection for a microfluidic system involves a single photodiode which is bonded onto a microfluidics chip as disclosed in the article entitled "An Optical MEMS-based Fluorescence Detection Scheme with Applications to Capillary Electrophoresis," by K. D. Kramer et al. (*SPIE Conference on Microfluidic Devices and Systems*, September 1998, SPIE Vol. 3515, pages 7–85.) Although a single photodiode is bonded onto the microfluidics chip, the photodiode is simply an electrical transducer and has no electronics signal processing or system control capability.

As described in the article entitled "Microfabricated Devices for Genetic Diagnostics," by Carlos H. Mastrangelo et al. (*Proceedings of the IEEE*, Vol. 86, No. 8, August 1998, pages 1769–1787), electronics have also been integrated directly onto the same substrate as a microfluidic system. Mastrangelo et al. have included the following devices on a silicon substrate: fluidic components, electrical driving components, diode detection components, and fluidic control elements (e.g., thermal valving). Although Mastrangelo et al. disclose integrated microfluidic and electronic components, the microfluidic and electronic components are fabricated on the same substrate. Fabricating both microfluidic and electronic components on the same substrate is not only more costly and difficult than fabricating microfluidic components, but also limits the selection of materials and processes available to fabricate the components. Further, the quality of the fabricated components is more easily controlled when the components are fabricated separately using known techniques.

Microfluidic systems have been fabricated in polymer, glass, silicon, and ceramic substrates. A microfluidic component fabricated on or in silicon can have electrical and data analysis components fabricated directly onto the silicon substrate as described by Mastrangelo, et al. However, this is not easily achieved on polymer or glass substrates. Polymer and glass substrates are the most useful substrates for microfluidic applications and therefore it is desirable to integrate polymer or glass substrates with electronics components. In view of the need to have electronics components in close proximity with microfluidic components and in view of the preference for polymer or glass microfluidic substrates, what is needed is a microfluidic system having a microfluidic component, ideally formed of polymer or glass, that is integrated with an electronics component.

SUMMARY OF THE INVENTION

A microfluidic component having a microfluidic channel is bonded to an electronics component having a circuit for processing signals related to the microfluidic component. In one embodiment, the electronics component is a prefabricated integrated circuit chip that includes signal processing and/or process control circuits that provide a substantially higher degree of functionality than a mere photodiode. The microfluidic component of the invention is preferably made of polymer and the integrated circuit chip is preferably bonded to the microfluidic component using a flip chip type process, common to the integrated circuit industry. The bonding of the microfluidic component to the electronics component provides a modular architecture in which different combinations of microfluidic components and electronics components can be used to create customized processing and analysis tools.

In a preferred embodiment, the microfluidic component includes a substrate that has features such as microfluidic channels, microfluidic compartments, and microfluidic flow control elements. Therefore, the microfluidic component may include known features such as capillary channels, separation channels, detection channels, valves and pumps. The microfluidic component may be fabricated by direct means such as photolithographic processes, wet or dry chemical etching, laser ablation, or traditional machining. The microfluidic component may also be fabricated by indirect means such as injection molding, hot embossing, casting, or other processes that utilize a mold or patterned tool to form the features of the microfluidic component. The microfluidic substrate is made of a material such as polymer, glass, silicon, metal, or ceramic. A polymer such as polyimide or polymethylmethacrylate (PMMA) is preferred. The microfluidic component is substantially fabricated before the electronic component is bonded to it.

In addition to the microfluidic features, the microfluidic component may include conductive traces that are formed within the substrate and/or on the surface of the substrate. The conductive traces provide electrical connection between the electronics component and various electrical features on or in the microfluidic component. These electrical features may include: (1) direct contacts to the fluid; (2) elements which, either in contact with or not in contact with the fluid, control the flow or the operation of the fluid or its contents; (3) sensors in direct contact with the fluid; (4) sensors that do not directly contact the fluid; (5) electrical heating or cooling elements integrated in or on the microfluidic component; (6) elements that can affect surface change within the microfluidic component; and (7) active microfluidic control elements such as valves, pumps, and mixers. Conductive traces may also lead to contact pads on the microfluidic component that provide electrical connections to off-component systems such as signal processors, signal readout devices, power supplies, and/or data storage systems. Providing contact pads on the microfluidic component for connection to off-component systems may eliminate the need to provide such contact pads on the electronics component.

While the electronics component may be composed of discrete electrical elements on a common substrate, such as a conventional printed circuit board, the component is preferably a prefabricated integrated circuit that may perform any of a variety of functions. The prefabricated integrated circuit may include a combination of op-amps, transistors, diodes, multiplexers, switches, filters, etc., that perform functions such as signal detection, signal processing, buffering, and/or control functions. The electronics component can be, for example, an application specific integrated circuit (ASIC). The electronics component is preferably connected to the microfluidic component using a flip-chip connection such as solder-bump attachment, gold-plating attachment, or electrically conductive adhesive attachment. Preferably, this component is an electrical component that is mounted within the area of the microfluidic component, such that there is no overhang by the electrical component over the side of the microfluidic component. However, a cantilevered electronics component may be used as a means of exposing contact pads for direct connection of the electronics component to an off-component system. As an alternative to the integrated circuit chip, the electronics component consists of discrete electrical devices mounted on a suitable substrate, such as a printed circuit board, which is then bonded to the microfluidic component using one of the above methods.

Similar to the microfluidic component, the electronics component is fabricated in a separate operation utilizing either conventional semiconductor processing techniques or assembly of discrete electrical elements such as resistors, capacitors, operational amplifiers, and the like. The electronics component may include a combination of memory, signal detection, signal processing, and control circuitry. The signal detection circuitry may detect electrical fields, magnetic fields, conductivity, resistivity, electrical current, dielectric constants, chemical properties, temperature, pressure, and/or light, depending on the operational requirements of the microfluidic component. The signal processing circuitry may, for example, amplify a signal, filter a signal, convert a signal from analog to digital, and/or make logical decisions based upon signal inputs. The control circuitry may provide voltage control, current control, temperature control, and/or clock signal generation.

Because the microfluidics component and the electronics component are separate devices, the electronics component can be bonded to the microfluidic component in various locations. For example, the electronics component can be bonded to the microfluidics component such that it is not directly over any microfluidic channels or chambers. Alternatively, the electronics component can be bonded to the microfluidics component such that it is directly over a microfluidic channel or chamber so as to provide direct signal detection by the electronics component over the channel, chamber, or other feature. As another possibility, the system may include more than one electronic component bonded on the same side or on opposite sides of the microfluidic component.

In one embodiment of the invention, the electronics component functions to provide an on-system feedback loop between the microfluidic component and the electronics component. For example, the electronics component can signal a heater to monitor the temperature at a particular area of the microfluidic component. In response to the monitored temperature, the electronics component can adjust the temperature on the microfluidics component as needed to achieve or maintain a desired condition. Other on-system process controls can be implemented between the microfluidic component and the electronics component to provide functionality and/or enhanced performance.

Since the electronics component and the microfluidic component are separate devices that are bonded to each other, the components can be manufactured separately utilizing quality control procedures that are specific to each type of component. In addition, because the electronics component and the microfluidic component are separate devices, the components can be interchanged with other microfluidic and electronics components to create customized processing and analysis tools. For example, different integrated circuits can be utilized with a single design of microfluidics component to create new systems.

DETAILED DESCRIPTION

Figure 1:
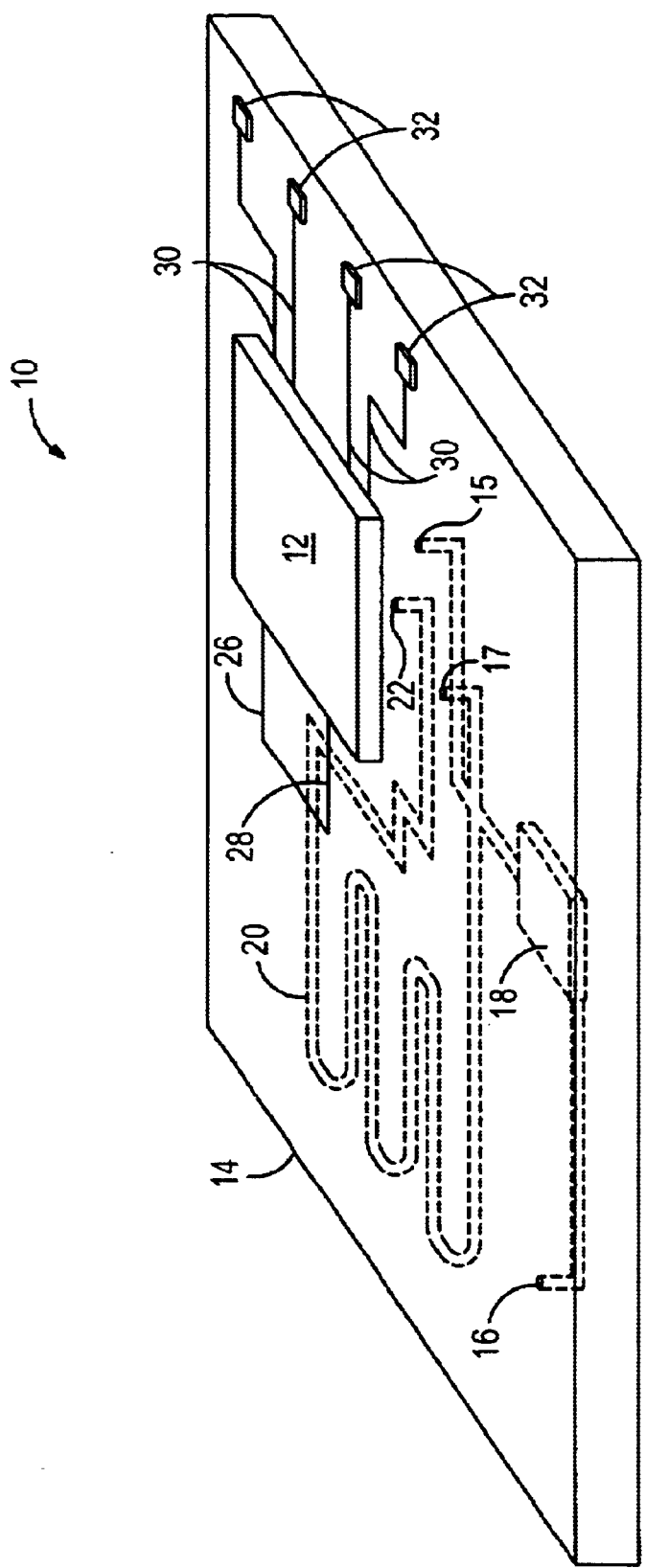
FIG. 1 is a perspective view of an integrated microsystem that includes an electronics component bonded to a microfluidic component, in accordance with one embodiment of the invention wherein the electronics component is not located above a microfluidic channel.

FIG. 1 is a view of an integrated microsystem 10 that includes an electronics component 12 that is bonded to a microfluidic component 14. The microfluidic component includes a substrate that has features such as microfluidic channels, microfluidic compartments, and microfluidic flow control elements. The microfluidic channels include features such as, but not limited to, simple fluidic transfer channels, separation channels, mixing channels, and the like. The microfluidic compartments can be considered to be fluid treatment compartments in which particular processes are performed. Such processes include, but are not limited to, mixing, labeling, filtering, extracting, precipitating, digesting, and the like. Microfluidic flow control elements include, but are not limited to, mixers, valves, pumps, pressure regulators, mass flow regulators, and the like. The microfluidic component also includes features such as input and output ports for fluidic communication with off-component devices or components.

The microfluidic component may be fabricated by direct means such as photolithographic processes, wet or dry chemical etching, laser ablation, or traditional machining. The microfluidic component may also be fabricated by indirect means such as injection molding, hot embossing, casting, or other processes that utilize a mold or patterned tool to form the features of the microfluidic component.

The microfluidic substrate is made of a material such as polymer, glass, silicon, or ceramic. Polymers are the preferred substrate materials, with polyimide being most preferred. Polymer materials particularly contemplated herein include materials selected from the following classes: polyimide, PMMA, polycarbonate, polystyrene, polyester, polyamide, polyether, polyolefin, or mixtures thereof.

Throughout the application, the term "microfluidic" refers to a component or system that has channels and/or chambers that are generally fabricated on the micron or submicron scale. For example, the typical channels or chambers have at least one cross-sectional dimension in the range of about 0.1 microns to about 500 microns.

Referring specifically to FIG. 1, the microfluidic component 14 is a planar device that includes an internal fluid treatment compartment 18 having input/output ports 15 and 16 and further includes an internal separation chamber 20 having input/output ports 17 and 22. The fluid treatment compartment and the separation chamber are shown as dashed lines, since they are formed within the microfluidic component 14. The dashed lines are interrupted at the intersection of the channel from compartment 18 with the channel from the separation channel 20, because the two channels intersect. The term "fluid treatment compartment" is used herein to describe a portion of the microfluidic component in which particular sample preparation processes are performed. Such processes include, but are not limited to, mixing, labeling, filtering, extracting, precipitating, digesting, and the like. The microfluidic component also includes conductive traces 26, 28, and 30 that are formed within the substrate and/or on the surface of the substrate. For example, the conductive traces 26 and 28 may be used to measure conductivity of a subject material at a point along the separation channel. The conductive traces 26 and 28 extend to the electronics component 12, which is bonded to the microfluidic component 14. The microfluidic component also includes conductive traces 30 that connect the electronics component to contact pads 32. The contact pads may provide electrical connections to off-chip systems such as signal processors, signal readout devices, a power supply, and/or data storage systems. Providing input/output contact pads on the microfluidic component eliminates the need to provide such contact pads on the electronics component.

The microfluidic component 14 is a device that is fabricated separately from the electronics component 12. That is, the microfluidic component is not fabricated by depositing a series of layers on top of or in conjunction with the electronics component.

The electronics component 12 is a prefabricated integrated circuit that may perform any of a variety of functions. Alternatively, the electronics component is a set of discrete electronic components mounted on an appropriate substrate, such as a conventional printed circuit board or the like. The term "electronics component" is used herein to refer to a device that is primarily electronic in nature and performs one or more of the operations to be described immediately below. In contrast to the above-cited system of Kramer et al., which discloses only a simple photodiode bonded to a microfluidic component, the electronics component of FIG. 1 has circuitry (not shown) that may include a combination of op-amps, transistors, diodes, multiplexers, switches, filters, logic, digital-to-analog converters, analog-to-digital converters, etc., that perform functions such as signal detection, signal processing, buffering, and/or signal or flow control. The electronics component is preferably electrically connected to the fluid component using a flip-chip connection, such as solder-bump attachment, gold-plating attachment, or electrically conductive adhesive attachment. In the preferred embodiment, the electronics component resides entirely within the area of the microfluidic component, such that there is no overhang of the electronics component beyond the edge of the microfluidic component. Alternatively, the electronics component consists of discrete electrical devices mounted on a suitable substrate which is then bonded to the microfluidic component using known techniques. The electronics component is fabricated separately from the microfluidic component utilizing conventional semiconductor processing techniques.

The electronics component 12 may include signal detection circuitry. The signal detection circuitry may detect electrical fields, electrical current, temperature, conductivity, resistivity, magnetic fields, dielectric constant, chemical properties, pressure, or light, depending on the operational requirements of the microfluidic component. The techniques utilized for detection of these properties are known in the microfluidics and electronics art and are not described further. It should be understood that circuitry for detecting other phenomena may also be included within the electronics component.

The electronics component 12 may also include signal processing circuitry. For example, the signal processing circuitry may amplify a signal, filter a signal, convert a signal from analog to digital, and make logical decisions based upon signal inputs. Because the possibilities for signal processing are numerous, it should be understood that any type of signal processing is anticipated for implementation in the electronics component.

The electronics component 12 may also provide circuitry for control functions such as voltage control, current control, temperature control, clock signal generation, etc. For example, the electronics component may convert power incoming to the system at 15 volts into 5 volts for utilization by the electronics component. The electronics component may also be utilized to create certain desired signals, such as sinusoidal signals. Flow control circuitry may be incorporated in order to manipulate microfluidic flow control elements of the type previously identified (e.g., valves, pumps, and regulators). As with the detection and processing circuitry, the possibilities for control circuitry are numerous and therefore it should be understood that any type of control circuitry is anticipated for implementation in the electronics component.

The electronics component 12 may also contain software or firmware that, through its operation, guides or controls the action of the circuitry. For example, the electronics component may contain programmable logic which allows a programmed algorithm to be executed so as to perform certain functions. These functions may include signal filtration, signal feedback, control operations, signal interruption, and other forms of signal processing.

The electronics component 12 is preferably an integrated circuit that is bonded to the microfluidic component 14. Bonding the microfluidic component to the electronics component may involve utilizing contact solder to connect corresponding electrical contact points on the microfluidics component and the integrated circuit. The contact solder can be tailored to the maximum temperature that can be withstood by the microfluidic substrate. Alternatively, gold contact bumps, gold contact pads, or conductive adhesive may be used to provide electrical contact between the electronics and microfluidic components. The bonding of the electrical component to the microfluidic component may be performed using a non-conductive adhesive or bonding method. The microfluidic component may include contact pads 32 that connect the integrated circuit to remote (off-component) systems. Although the microfluidic component of FIG. 1 includes the contact pads to connect the integrated circuit to remote systems, other arrangements are possible where the contacts are integrated onto the electronics component.

In another embodiment, the electronics component 12 may provide all of the electrical functions of the system, while the microfluidic component has no electrically conductive features. For example, the electronics component may contain all of the off-system electrical connections, all of the electrical, photo, physical, or chemical sensors, all of the signal processing circuitry, and all of the data connections. In this embodiment, the electronics and microfluidic components need only be attached mechanically, since no electrical interconnection is required.

Figure 2:
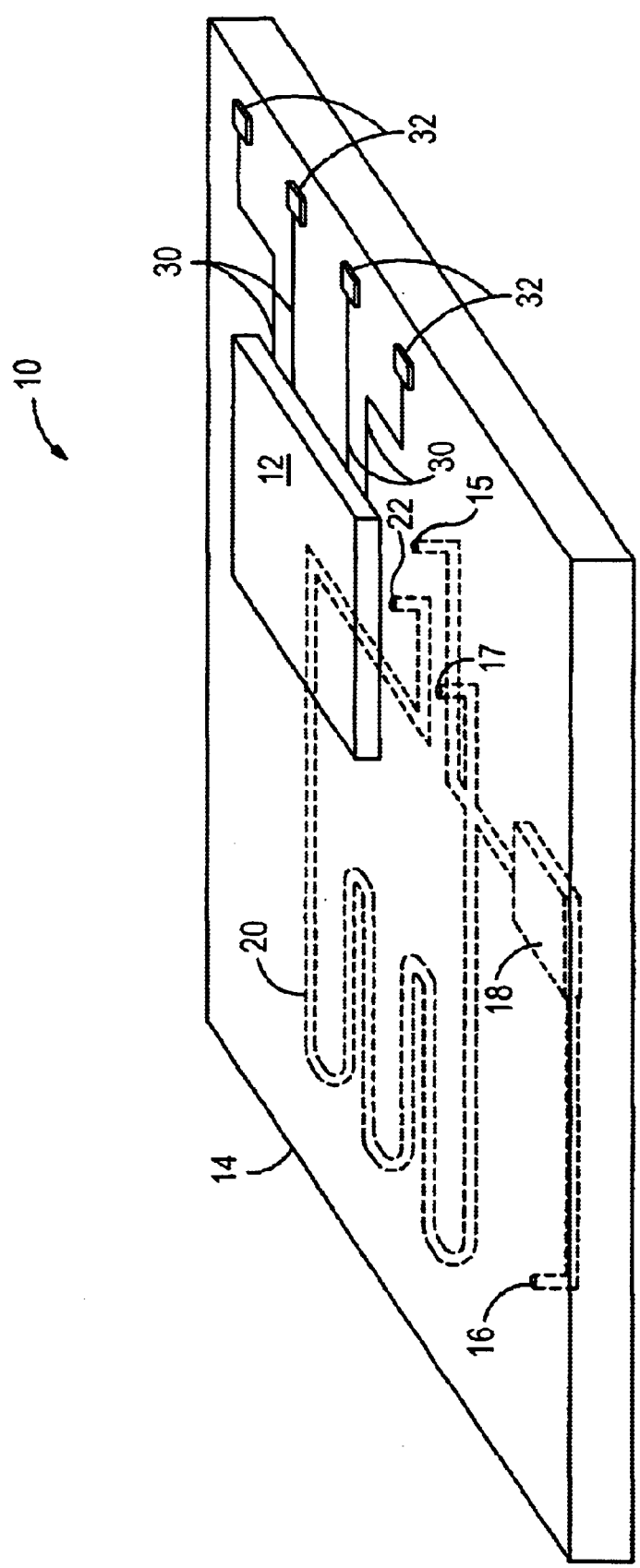
FIG. 2 is a perspective view of an integrated microsystem that includes an electronics component bonded to a microfluidic component in accordance with a second embodiment of the invention, wherein the electronics component is attached directly above a microfluidic channel.
Figure 3:
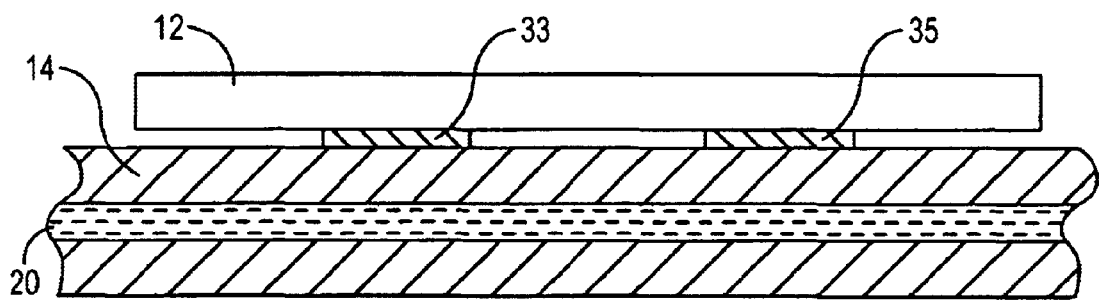
FIG. 3 is a side sectional view of a portion of the integrated microsystem of FIG. 2.

The electronics component 12 can be bonded to the microfluidic component in various locations. As shown in FIG. 1, the electronics component is not located directly over any microfluidic channels or chambers. When the electronics component is not located directly over a microfluidic channel or chamber, the placement of the electronics component can be made with minimum accuracy, since only electrical contact pad alignment is necessary. For example, a placement tolerance of around 50 to 200 micrometers is acceptable. The integrated circuit can alternatively be located directly over a microfluidic channel or chamber in order to provide direct signal detection by a detection device that is integrated into the electronics component. FIGS. 2 and 3 illustrate an arrangement wherein the electronics component 12 is flip-chip bonded directly over the separation channel 20 within the microfluidic component 14. Referring specifically to FIG. 3, the electronics component 12 may be used to measure the conductivity of the fluid within the separation channel 20. The electronics component contacts the surface of the microfluidic component 12 at a pair of conductive members 33 and 35, such as contact pads. Each contact pad is capacitively coupled to the fluid within the separation channel, since the substrate material of the microfluidic component is a dielectric between two conductive materials. If one of the contact pads is connected to a source of alternating current and the other contact pad is connected to a detector, the conductivity of the fluid may be measured. The circuitry for monitoring the dynamic conductivity of the fluid is at least partially contained within the electronics component 12.

Figure 4:
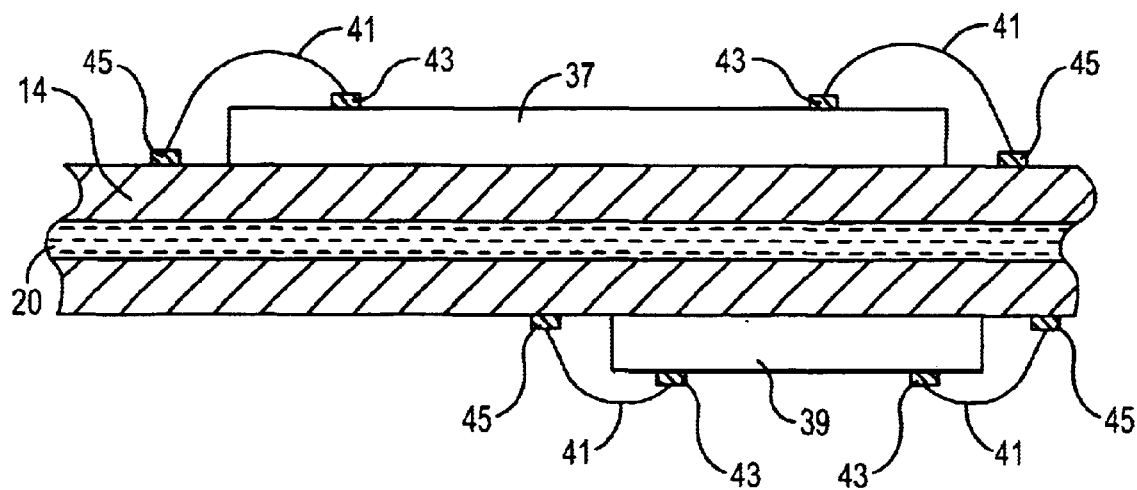
FIG. 4 is a side sectional view of an alternative means for connecting an electronics component to a microfluidic component.

It is possible to have more than one electronics component bonded to the microfluidic component. Referring now to FIG. 4, two electronics components 37 and 39 are shown bonded to opposite sides of the substrate which forms the microfluidic component 14. Conventional bond wires 41 may be used to provide electrical connection between contact pads 43 on the electronics components and contact pads 45 on the microfluidic component, but other techniques for electrically connecting the components may be employed. As one possible example, the component 39 may be an integrated circuit chip that is specific to microfluidic control functions and component 37 may be another integrated circuit chip that is specific to signal processing functions.

Returning to FIGS. 1 and 2, in one embodiment of the integrated microsystem 10, the electronics component 12 functions to provide a feedback loop between the microfluidic component 14 and the electronics component. For example, the temperature of a region on the microfluidic component can be monitored by the electronics component. In response to the measured temperature, the electronics component can adjust the temperature of the monitored region on the microfluidic component as needed to achieve or maintain the desired temperature. The feedback between the microfluidic component and the electronics component is useful with, for example, processing or analysis techniques that require multiple temperature changes. Although temperature control is described as a specific example of a feedback implementation, other on-system feedback loops can be implemented between the microfluidic component and the electronics component to provide enhanced performance. Providing signal processing within the integrated circuit that is flip-chip bonded to the microfluidic component enables control of various processes, such as measurement, reaction, concentration, or separation processes.

An advantage of bonding an electronics component to a microfluidic component is that the two components make up a modular architecture in which each component can be separately manufactured. Electronics and fluidic components require different materials and methods of manufacture. Separating their manufacture eliminates the difficulties of integrating the fabrication processes and different materials. Further, manufacturing the electronics component separately from the microfluidic component enables quality control procedures to be specific to the type of device that is being manufactured. For example, the environmental control requirements for integrated circuit fabrication are not the same as for microfluidic component fabrication. In addition, because the electronics component and the microfluidic component are separately manufactured, the two components are interchangeable with other microfluidic components and electronics components. For example, the same design microfluidic component can be equipped with different electronics components to accomplish different goals. By using the same microfluidic component to create systems having different capabilities, the cost of microfluidic component development is avoided, while flexibility in processing and control is enabled.

Figure 5:
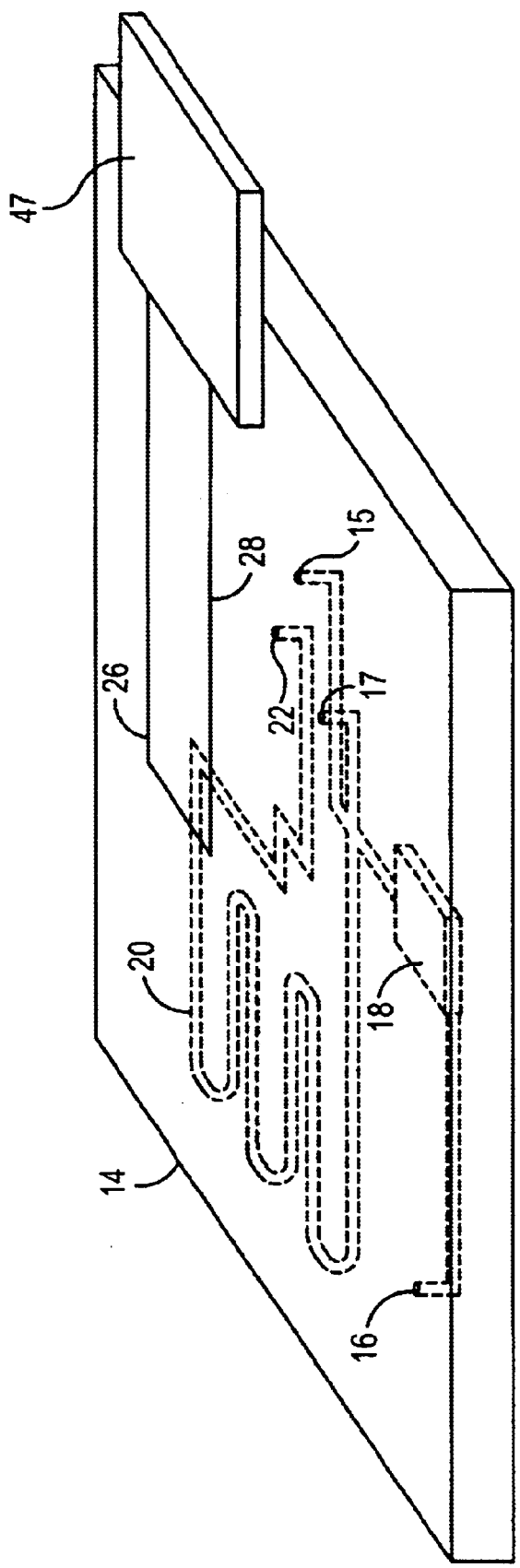
FIG. 5 is a top perspective view of an integrated microsystem that includes a cantilevered electronics component in accordance with another embodiment of the invention.
Figure 6:
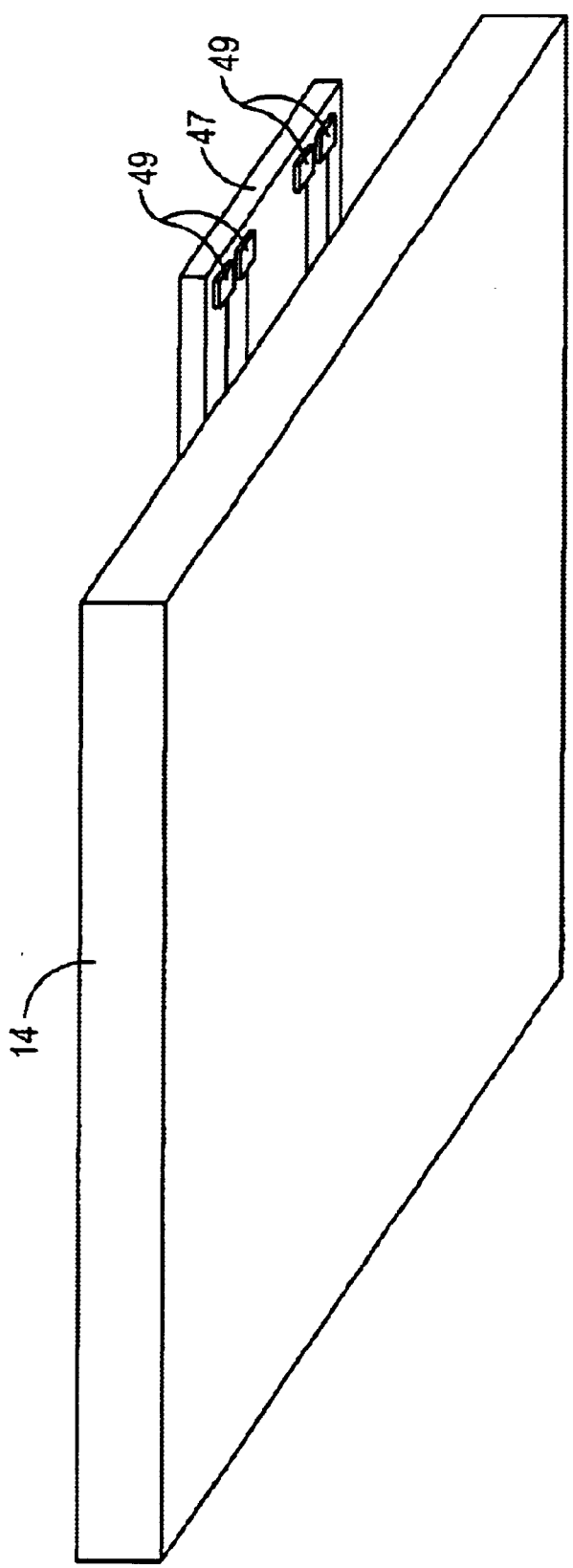
FIG. 6 is a bottom perspective view of the integrated microsystem of FIG. 5.

Another embodiment of the invention is shown in FIGS. 5 and 6. In this embodiment, the electronics component 47 is cantilevered from the edge of the substrate that forms the microfluidic component 14. The advantage of this embodiment is that the contact pads 49 on the lower surface of the electronics component are exposed, allowing direct connections to off-system circuitry. That is, the traces 30 and contact pads 32 of FIG. 1 are not required. Optionally, the cantilevered electronics component 47 may extend over a microfluidic channel or compartment and perform functions (e.g., temperature monitoring) that do not require any electrical connections between the electronics component 47 and the microfluidic component 14. Thus, the conductive traces 26 and 28 of FIG. 5 would not be necessary, but the electronics component would extend over a portion of the separation channel 20 or the fluid treatment compartment 18.

Figure 7:
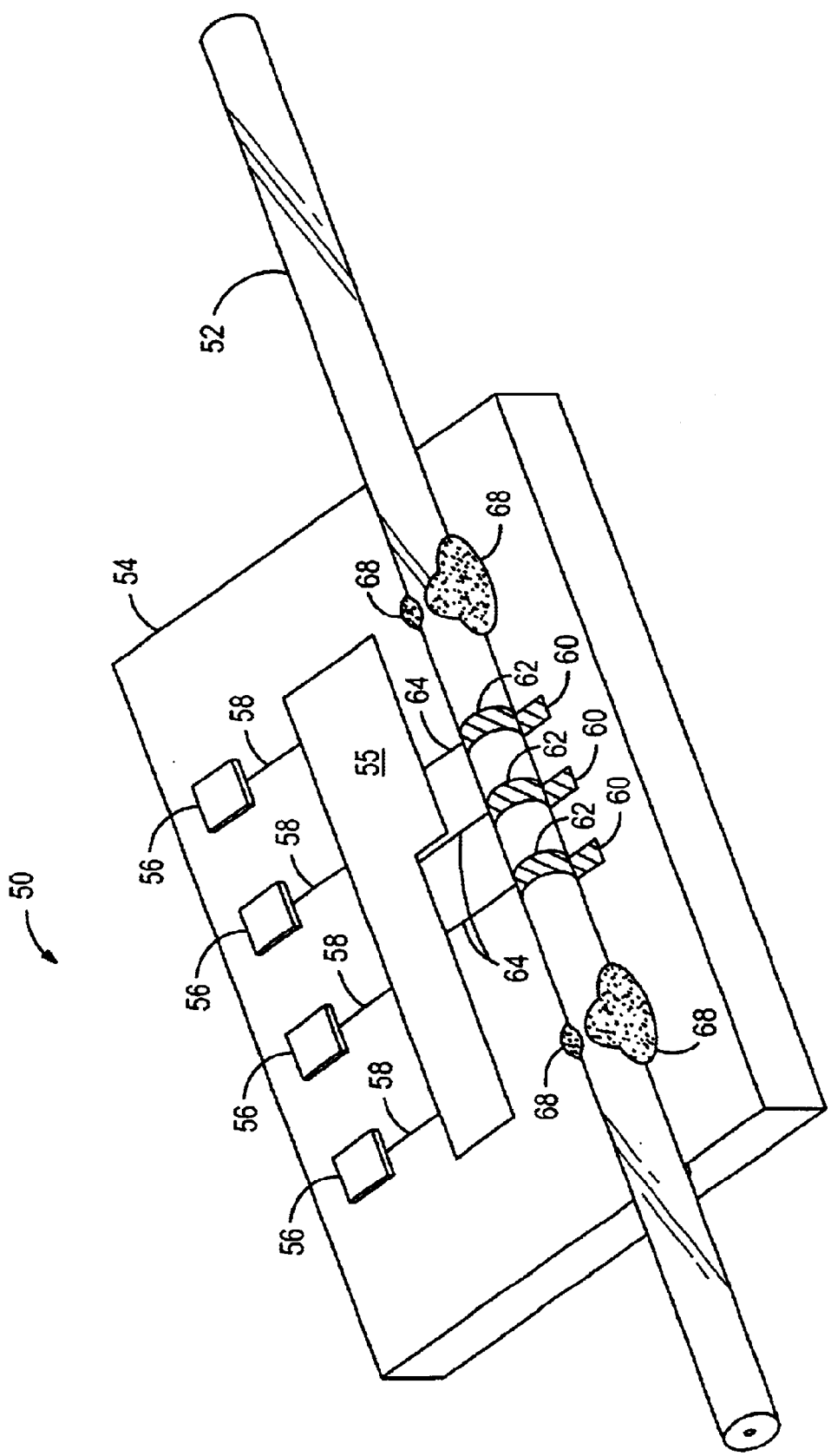
FIG. 7 is a perspective view of an integrated microsystem that includes a semiconductor substrate that is bonded to a capillary tube in accordance with the invention.

FIG. 7 is a depiction of an alternative embodiment of an integrated microsystem 50 In accordance with the invention. The integrated microsystem includes a microfluidic component in the form of a capillary tube 52 that Is bonded to a semiconductor substrate 54. The semiconductor substrate includes on-chip circuitry 55 which may perform any of the functions described above with reference to FIGS. 1 and 2. The semiconductor substrate may also Include contact pads 56 and conductive traces 58 for connecting the on-chip circuitry to a remote system. The semiconductor substrate also Includes capillary contact pads 60 which provide electrical contact between the semiconductor substrate and contact pads 62 which are formed on the capillary tube. The contact pads 60 on the semiconductor substrate are connected to the on-chip circuitry by additional conductive traces 64.

As shown in FIG. 7, the capillary tube 52 is bonded to the silicon substrate 54 with bonding material 68 such that the contact pads 60 from the semiconductor substrate are aligned with the contact pads 62 on the capillary tube. Alternatively, conductive adhesive may be used to directly bond conductive features on the components to each other. Connecting the capillary tube onto the same substrate that includes the on-chip circuitry 56 allows detection and analysis of the fluids within the capillary tube to be performed with all of the advantages and capabilities described above with reference to FIGS. 1 and 2. The integrated microsystem 50 of FIG. 7 can be utilized in, for example, capillary electrophoresis.

Figure 8:
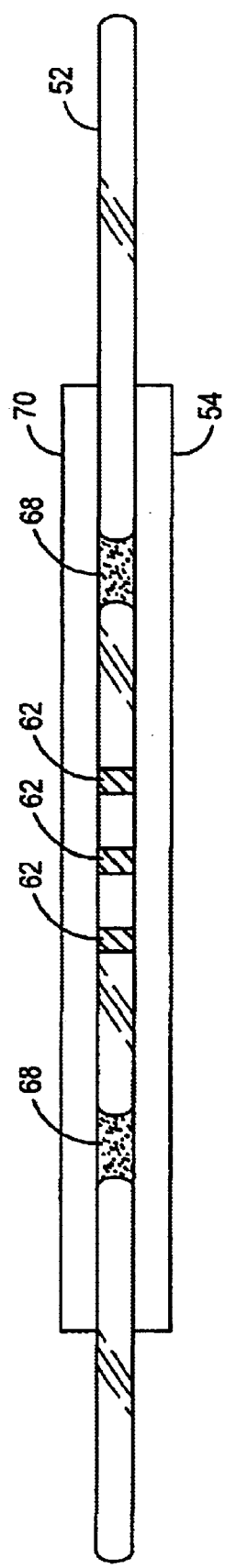
FIG. 8 is a side view of the semiconductor substrate and capillary tube shown in FIG. 3 with an additional semiconductor substrate attached to the capillary tube opposite the first semiconductor substrate in accordance with the invention.

In an alternative embodiment, a second semiconductor substrate can be bonded on top of the capillary tube 52 shown in FIG. 7. FIG. 8 depicts a side view of two planar semiconductor substrates 54 and 70 bonded onto opposite sides of the capillary tube with bonding material 68, such as a glue or solder. The electrical contact points between the semiconductor substrates and the capillary tube can be distributed between the two substrates as needed. For example, the leftmost capillary contact pad 62 may be electrically connected to the top substrate 70 and related circuitry and the two rightmost capillary contact pads may be electrically connected to the bottom substrate 54 and related circuitry. An additional advantage of this embodiment of the invention is that there is enhanced protection of the active sections of both the electronics and the capillary tube.

What is claimed is:

1. An integrated microsystem comprising:
   a prefabricated microfluidic component having microfluidic features for processing a fluid of interest; and
   an electronics component having signal detection and signal processing circuitry so as to evaluate a property of said fluid of interest, said electronics component and said prefabricated microfluidic component being first and second devices that are bonded together to provide a modular architecture, said electronics component being bonded to said prefabricated microfluidic component along exterior surfaces of said electronics and prefabricated microfluidic components such that said exterior surfaces face each other along at least one bond region, said electronics component also being structurally independent of any said microfluidic feature;
   wherein said electronics component is an integrated circuit chip that is flip chip bonded to said prefabricated microfluidic component.

2. The integrated microsystem of claim 1 wherein said electronics component is formed of discrete electronic devices on a substrate that is bonded to said prefabricated microfluidic component.

3. The integrated microsystem of claim 1 wherein said circuitry of said electronics component has an output for providing direct feedback to said prefabricated microfluidic component in response to signals from said circuitry, thereby creating a feedback loop that is isolated within said integrated microsystem.

4. The integrated microsystem of claim 1 wherein said electronics component includes a signal amplifier circuit for amplifying a signal from a signal detection subcircuit of said circuitry.

5. The integrated microsystem of claim 1 wherein said electronics component includes firmware for signal processing and signal control on-board said electronics component.

6. The integrated microsystem of claim 1 wherein said electronics component is bonded to said prefabricated microfluidic component such that a detector element is directly above at least one of said microfluidic features of said prefabricated microfluidic component.

7. The integrated microsystem of claim 1 further comprising a second electronics component bonded to said prefabricated microfluidic component.

8. The integrated microsystem of claim 7 wherein said electronics component and said second electronics component are on opposite sides of said prefabricated microfluidic component.

9. An integrated microsystem comprising:
   a microfluidic component having microfluidic features, including a processing region for processing a fluid of interest, said microfluidic component being a first device having first and second outer surfaces, said first outer surface having a first plurality of contact pads; and
   an electronics component that is a second device bonded to said microfluidic component and having third and fourth outer surfaces, said third outer surface having a second plurality of contact pads, said microfluidic component being bonded to said electronics component, said electronics and microfluidic components being electrically and mechanically linked by electrically conductive material connecting said first and second pluralities of contact pads, said electronics component having circuitry to control a process within said microfluidic component, but being structurally independent of said microfluidic features.

10. The integrated microsystem of claim 9 wherein said circuitry of said electronics component enables control of at least one of a reaction, concentration, or separation process that occurs within said microfluidic features of said microfluidic component.

11. The integrated microsystem of claim 9 wherein said circuitry of said electronics component enables control of the flow of fluids within said microfluidic component.

12. The integrated microsystem of claim 9 wherein said circuitry of said electronics component enables at least one of voltage control, current control, electrical field control, and magnetic field control.

13. The integrated microsystem of claim 9 wherein said circuitry of said electronics component further enables signal processing of signals generated by said electronics component in cooperation with said microfluidic component.

14. A method for forming a microsystem comprising:

providing an electrical circuit-containing device that includes signal processing circuitry, said electrical circuit-containing device having a first surface and being exclusive of any microfluidic feature;

providing a microfluidic device that includes microfluidic features for processing a fluid of interest, said microfluidic device having a second surface and being a discrete device from said electrical circuit-containing device, such that said microfluidic features are structurally independent of said circuit-containing device; and bonding said electrical circuit-containing device to said microfluidic device at said first and second surfaces such that properties of said fluid of interest in said microfluidic features can be evaluated by said signal processing circuitry.

* * * * *